United States Patent

Sembert

[11] Patent Number: 5,716,319
[45] Date of Patent: Feb. 10, 1998

[54] METHOD OF DELAYING EJACULATION DURING SEXUAL INTERCOURSE

[76] Inventor: George P. Sembert, 6300 Tamannary Dr., Greensboro, N.C. 27455

[21] Appl. No.: 635,369

[22] Filed: Apr. 19, 1996

[51] Int. Cl.⁶ .................................................. A61F 5/00
[52] U.S. Cl. ........................ 600/38; 607/108; 607/112; 607/114
[58] Field of Search ......................... 600/38, 39, 41; 607/96, 108, 112, 114, 143; 128/898

[56] References Cited

U.S. PATENT DOCUMENTS

| | | | |
|---|---|---|---|
| 4,253,464 | 3/1981 | Zorgniotti | 607/104 |
| 5,063,939 | 11/1991 | Walston | 600/38 |
| 5,152,285 | 10/1992 | Gregy | 607/108 |
| 5,243,974 | 9/1993 | Allen | 607/108 |
| 5,545,199 | 8/1996 | Hudson | 607/114 |

*Primary Examiner*—John P. Lacyk
*Assistant Examiner*—Rosiland Kearney
*Attorney, Agent, or Firm*—Adams Law Firm, P.A.

[57] ABSTRACT

A sexual therapeutic device is provided for being worn by a male to delay ejaculation during sexual intercourse. The device includes a pouch for being positioned adjacent to the scrotum of the male. The pouch is adapted for receiving and holding the testicles when in a descended position. A cold compress is attached to the pouch and resides adjacent to the testicles when in an ascended position. The compress cools the testicles to delay ejaculation of the male during intercourse. A strap is attached to the pouch and extends around the penis of the male to hold the device in position during use.

6 Claims, 4 Drawing Sheets

METHOD OF DELAYING EJACULATION DURING SEXUAL INTERCOURSE

TECHNICAL FIELD AND BACKGROUND OF THE INVENTION

This invention relates to a sexual therapeutic device for a male, and method of delaying ejaculation during sexual intercourse. The invention is particularly useful in the treatment of premature ejaculation. Premature ejaculation is generally recognized as the most common sexual problem in men, and is especially common in adolescents. For many adult men, premature ejaculation often results from over stimulation or anxiety about sexual performance.

Ejaculation is defined as the emission of semen from the penis at orgasm. Ejaculation is a reflex action that depends on regular and rhythmic pressure on the penis, usually during intercourse or masturbation. This stimulation acts on spinal nerves and triggers ejaculation. Shortly before ejaculation, the muscles around the sperm ducts, the prostate gland, and the seminal vesicles contract rhythmically, forcing the sperm from the sperm ducts to move forward and mix with the secretions from the seminal vesicles and prostate. The testicles are involuntarily raised from a normal, descended position to an ascended position closely adjacent to the base of the penis. At ejaculation, this fluid is propelled through the urethra and out of the body. *Encyclopedia of Medicine*, 1989.

Some prior art therapies for treating premature ejaculation include the use of prescription drugs, such as beta blockers and antidepressants. These drugs typically produce unwanted side effects, and are therefore not practical solutions to this problem. Other treatments use a local anesthetic, such as benzocaine cream. Such anesthetics generally dull the sexual feeling in both partners, and are therefore also an inadequate solution. Sexual counseling is a further alternative, but is relatively expensive and not readily available to a majority of the public.

The present invention addresses these and other problems of the prior art by providing a sexual therapeutic device which is relatively inexpensive, reusable, and has no undesirable side effects. The device is quickly and conveniently put on, provides negligible discomfort, and contains no toxic materials or ingredients. Moreover, the device is adjustable to fit a given user, and can be tailored to any desired dimension.

SUMMARY OF THE INVENTION

Therefore, it is an object of the invention to provide a sexual therapeutic device for a male which acts to delay ejaculation during intercourse.

It is another object of the invention to provide a therapeutic device which is effective without producing any undesirable chemical side effects.

It is another object of the invention to provide a therapeutic device which is relatively inexpensive and easy to manufacture.

It is another object of the invention to provide a therapeutic device which contains no toxic materials or ingredients.

It is another object of the invention to provide a therapeutic device which is reusable.

It is another object of the invention to provide a therapeutic device which can be conveniently adjusted or tailored to comfortably fit a particular user.

It is another object of the invention to provide a method of delaying ejaculation of a male during sexual intercourse that does not require sexual counseling.

These and other objects of the present invention are achieved in the preferred embodiments disclosed below by providing a sexual therapeutic device for being worn by a male to delay ejaculation during sexual intercourse. The device includes a pouch for being positioned adjacent to the scrotum of the male. The pouch is adapted for receiving and holding the testicles when in a descended position. A cold compress is attached to the pouch and resides adjacent to the testicles when in an ascended position. The compress cools the testicles to delay ejaculation of the male during intercourse. A strap is attached to the pouch and extends around the penis of the male to hold the device in position during use.

According to one preferred embodiment of the invention, the pouch is made of leather.

According to another preferred embodiment of the invention, the cold compress is a sealed, flexible pack containing a refreezeable gel.

According to yet another preferred embodiment of the invention, the pack has an outer fabric layer for residing in skin contact adjacent to the testicles of the male in the ascended position.

According to yet another preferred embodiment of the invention, the outer fabric layer of the pack includes cotton fibers.

According to yet another preferred embodiment of the invention, the cold compress is attached to the pouch by sewing stitches.

According to yet another preferred embodiment of the invention, the strap includes adjustment means for adjusting the attachment of the device to the male.

An embodiment of the method according to the invention for delaying ejaculation during sexual intercourse comprises the steps of positioning a pouch of a sexual therapeutic device adjacent to the scrotum of a male. The pouch is adapted for receiving and holding the testicles when in a descended position. A cold compress is attached to the pouch and positioned adjacent to the testicles when in an ascended position. The compress cools the testicles to delay ejaculation of the male during intercourse. Attachment means are attached to the pouch for holding the device in position during use.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

Figure 1:
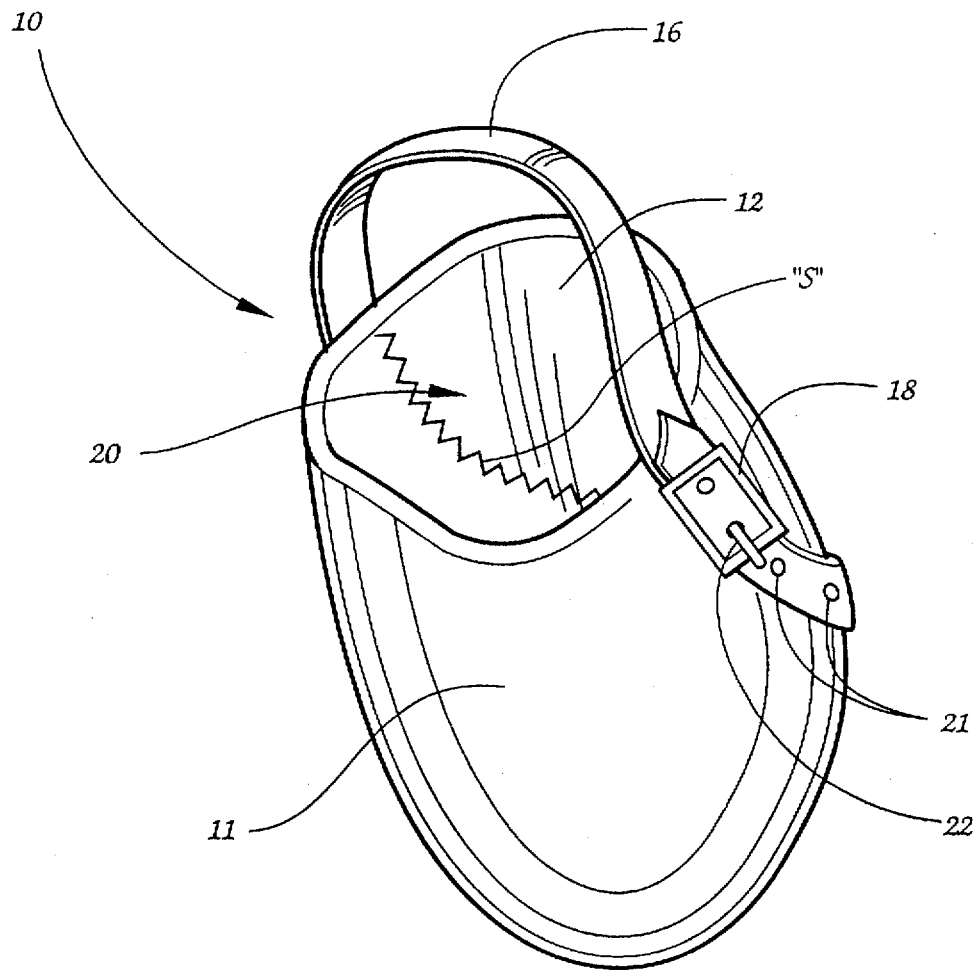
FIG. 1 is a perspective view of the sexual therapeutic device according to one preferred embodiment of the invention, and showing the strap fastened as worn by a user.

Referring now specifically to the drawings, a sexual therapeutic device according to the present invention is illustrated in FIG. 1 and shown generally at reference numeral 10. The device 10 is used by males to delay ejaculation during sexual intercourse, and specifically, to help remedy premature ejaculation.

Figure 2:
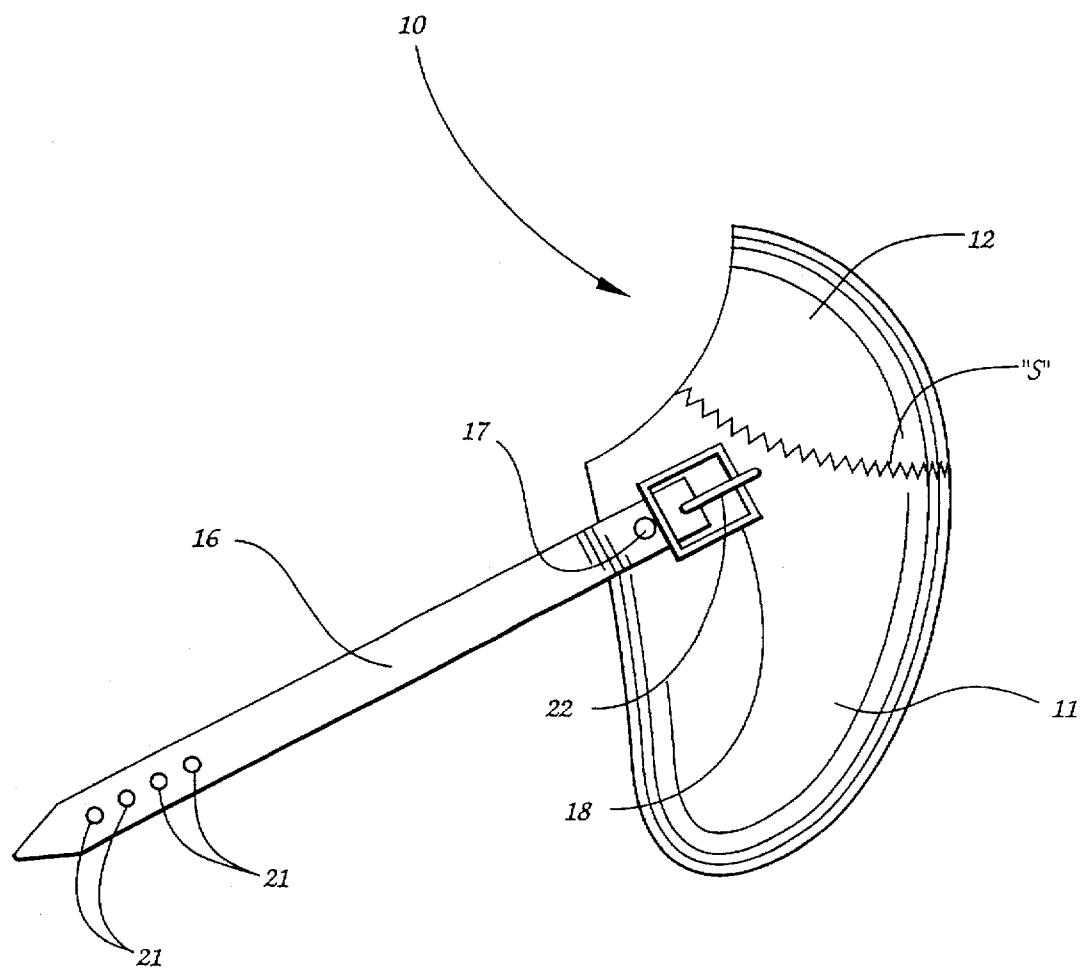
FIG. 2 is a side elevational view of the device.
Figure 3:
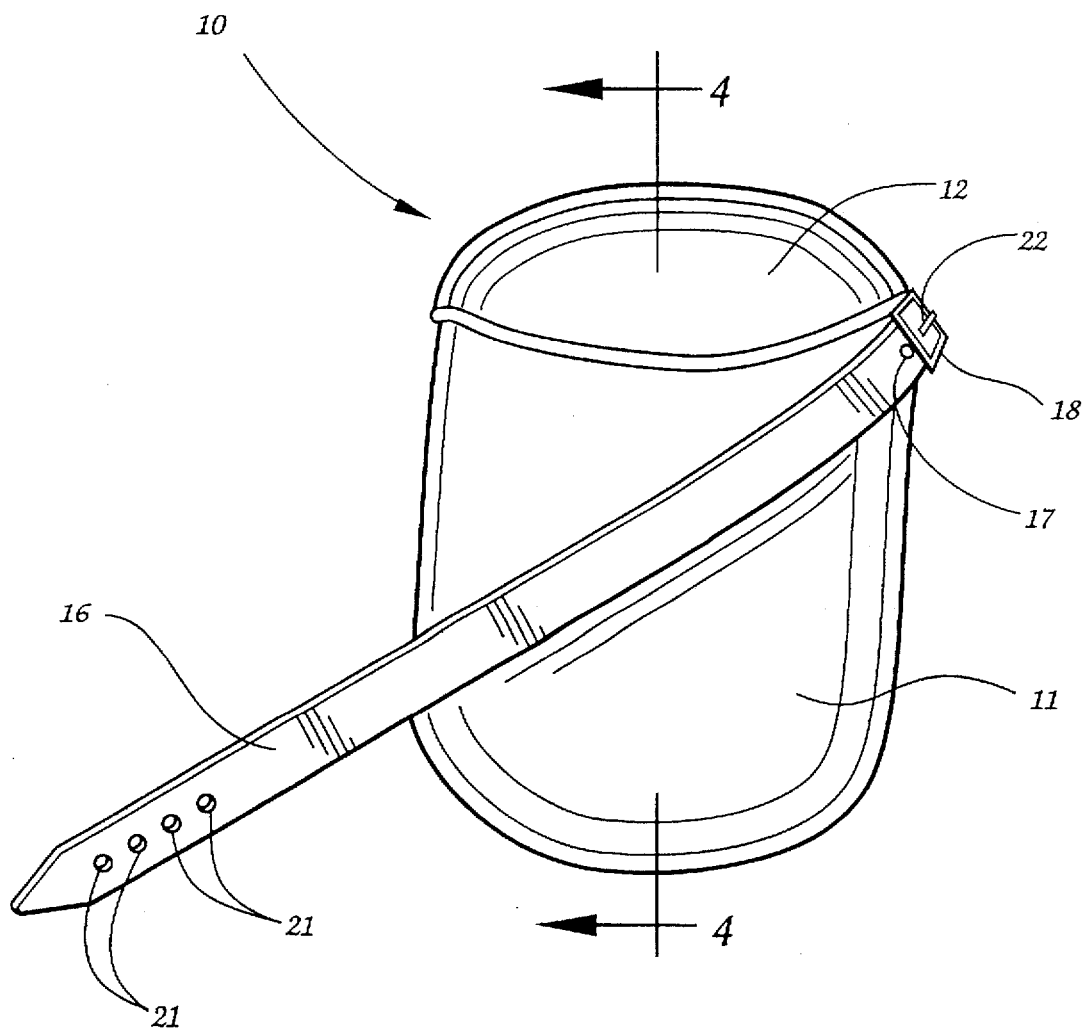
FIG. 3 is a front elevational view of the device.

As shown in FIGS. 1-3, the device 10 includes a pouch 11 of sufficient dimension to receive and comfortably hold the testicles of the wearer when in a normal, descended position. The pouch 11 is preferably made of soft flexible leather or other fabric material. A cold compress 12 is attached along a top perimeter of the pouch 11 by sewing stitches "S", and is located to reside immediately adjacent to the testicles when elevated to an ascended position during heavy sexual activity.

Figure 4:
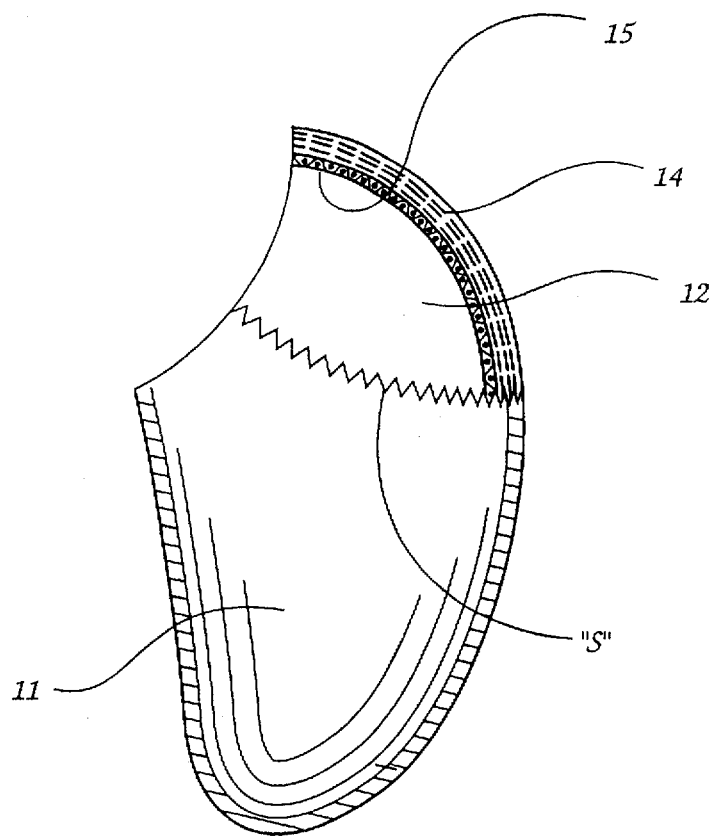
FIG. 4 is a cross-sectional view of the device taken substantially along lines 4—4 of FIG. 3.

Referring to FIG. 4, the cold compress 12 is a flexible, relatively thin sealed pack containing a refreezeable gel 14, and having an outer liner 15 constructed of one or more fabric layers for residing in skin contact with the wearer during use. The outer liner 15 may include cotton, polyester, or nylon fibers. According to one embodiment, the overall thickness of the cold compress 12 is between about 0.2 to 0.6 cm with the thickness of the pouch 11 being about 0.1 cm. For optimum effectiveness, the device 10 is preferably placed in a freezer approximately two hours before use to lower the temperature of the gel 14 to between −20 and 0 degrees C. An example of one suitable cold compress is described in U.S. Pat. No. 4,910,978, assigned to Becton, Dickson and Company of Franklin Lakes, N.J. The complete disclosure of this patent is incorporated herein by reference.

The pouch 11 is maintained in position during use by an adjustable, elongated strap 16 fixedly attached at one end to the pouch 11 by a rivet 17. The rivet 17 prevents rotational movement of the strap 16 relative to the pouch 11 as the device 10 is being put on and worn by the user. As best shown in FIG. 1, the strap 16 is intended to extend over the penis and around the back of the pouch 11 where it fastens to the pouch 11 with a conventional hook fastener 18. The penis extends through the open space 20 defined between the strap 16 and the front edge of the pouch 11. This space 20 is readily adjusted by the wearer, as desired, by selecting an appropriate hole 21 in the strap 16 through which the hook 22 of the fastener 18 is received. The male user can therefore properly fit the device 10 for wear in a secure and comfortable manner. Alternately, other fastening means not shown such as complementary hooks and loops may be used.

A sexual therapeutic device is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A method of delaying ejaculation during sexual intercourse, comprising the steps of:
    (a) positioning a pouch of a sexual therapeutic device adjacent to the scrotum of a male, said pouch being adapted for receiving and holding the testicles when in a descended position;
    (b) positioning cooling means comprising a refreezable gel in an area of said pouch adapted to reside adjacent to the testicles when in an ascended position to cool the testicles and thereby delay ejaculation of the male during intercourse; and
    (c) providing attachment means attached to said pouch for holding the device in position during use.

2. A method according to claim 1, wherein the cooling means comprises a cold compress.

3. A method according to claim 1, wherein the pack comprises an outer fabric liner for residing in skin contact adjacent to the testicles of the male in the ascended position.

4. A method according to claim 3, wherein the outer fabric liner of the pack comprises one or more layers of cotton fibers.

5. A method according to claim 1, wherein the pouch is made of leather.

6. A method according to claim 1, wherein the strap includes adjustment means for adjusting the attachment of the device to the male.

* * * * *